United States Patent [19]
McCullough, Jr. et al.

[11] Patent Number: 5,151,198
[45] Date of Patent: Sep. 29, 1992

[54] METHOD AND APPARATUS FOR SEPARATING FLUIDS USING A CARBONACEOUS POLYMERIC FILTER HAVING A LOI GREATER THAN 40

[75] Inventors: Francis P. McCullough, Jr., Lake Jackson; Stuart D. Stein, Freeport, both of Tex.

[73] Assignee: The Dow Chemical Company, Midland, Mich.

[21] Appl. No.: 581,339

[22] Filed: Sep. 11, 1990

[51] Int. Cl.$^5$ .................... B01D 39/08; B01D 39/16
[52] U.S. Cl. .................... 210/767; 210/243; 210/315; 210/489; 210/503; 55/187
[58] Field of Search ............... 210/188, 243, 314, 315, 210/488, 489, 492, 496, 497.2, 503, 767, DIG. 5, DIG. 6; 55/97, 185, 186, 187, 2, 487, 489, DIG. 17, DIG. 25; 428/284, 285, 368, 369

[56] References Cited

U.S. PATENT DOCUMENTS

| | | | |
|---|---|---|---|
| 4,948,515 | 8/1990 | Okumura et al. | 210/243 |
| 4,999,108 | 3/1991 | Koch et al. | 210/243 |
| 5,007,994 | 4/1991 | Snee | 210/243 |

Primary Examiner—Robert A. Dawson
Assistant Examiner—W. L. Millard

[57] ABSTRACT

An improvement in an apparatus for separating fluids or non-biotechnological products in solution, wherein said apparatus has a fibrous element which permits flow of fluids therethrough the improvement wherein the fibrous element is composed of non-flammable irreversibly heat set non-graphitic carbonaceous fibers having an LOI greater than 40.

17 Claims, 1 Drawing Sheet

METHOD AND APPARATUS FOR SEPARATING FLUIDS USING A CARBONACEOUS POLYMERIC FILTER HAVING A LOI GREATER THAN 40

FIELD OF THE INVENTION

The present invention relates to a novel fibrous element for use in separators for non-biotechnological products. More particularly, there is provided structures comprising non-graphitic carbonaceous fibers which are utilized in fluid separating devices or devices such as demisters, column separators, filtration apparatuses, electrophoresis apparatuses, and the like.

BACKGROUND OF THE INVENTION

Fibrous elements that work effectively in demisting, column packing and filtration applications ideally should possess at least some of the characteristics of being inert in the system of use, have a high temperature stability, a low pressure drop, not wetted and/or swollen by the fluid system in use, have good flame arresting properties in the presence of flammable fluids, have sufficient conductivity to render anti-static or grounding properties, can be used with an electrical field or gradient electrical field to enhance separation and have good vibration stability without vitrification with time at temperature. No single material or combination of materials prior to the present invention is capable of being customized to contain a desired combination of these properties.

Mist eliminator mesh pads are typically pads composed of elements, such as knitted wire mesh, and are commonly placed in a gas-liquid contact apparatus to remove mist from a mist-containing gas stream. Typically, such mist eliminator mesh pads are composed of fibrous or filament elements, such as four to fifteen mil diameter stainless steel wire, are arranged from about three to twenty-four inches in thickness, have a density ranging from about four to fifteen pounds per cubic foot and range in diameter from about one to thirty feet depending upon the gas-liquid contact apparatus in which the pads are employed Such mist eliminator mesh pads are generally effective in removing droplets as small as one to five micrometers from mist containing gas streams.

The capacity of a mist eliminator mesh pad in a gas-liquid contact apparatus, i.e. the maximum gas velocity of the gas stream through the mesh pad, is generally limited by the mesh pad's ability to drain rapidly the coalesced liquid collected by the mesh pad. One attempt to increase the capacity of mist eliminator mesh pads and to reduce the mesh pad's pressure drop has been the employment of drainage cylinders or ancillary rolls of wire mesh fixed to the bottom of conventional mist eliminator mesh pads. Such drainage cylinder of ancillary rolls is provide for localized, separate regions of flow interruption and interception, thereby creating a preferential drainage foci. (See for example U.S. Pat. No. 4,022,593, issued May 10, 1977, hereby incorporated by reference in its entirety.)

In some limited cases, it has been the past practice to employ variable high and low density mesh pads in a vapor phase intercept pattern to enhance mist elimination performance. In such cases, the lower portion of the mesh pad is formed of a low density material to promote rapid and easy draining of coalesced liquid and to aid in working away precipitated material from the pad, while the upper portion of the pad is formed of a high density material to collect liquid particulates from the upwardly flowing, mist containing vapor stream.

It is desirable to provide an improved mist eliminator mesh pad in order to improve the mesh pad capacity and to provide for reductions in pressure drop compared to conventional mesh pads.

There have been many recent advances in the use of pulsed field electrophoresis and the separation of molecules based on their migration through an electrical field. Electrophoresis separation is generally accomplished by establishing an electrical field between two electrodes in a gel such as an argose gel. Column separation of molecules has been accomplished using electrically conductive polymers such as polyethylene oxides or polypyrrole copolymers. However, such polymers and gels have only found limited application and cannot be utilized in many common solvent systems. Also, the prior conductive polymers do not provide a sufficient variant in pulsed fields to perform many simple separations.

There is a need to provide a means for separating molecules in solution, for example, removal of by products in chemical reactions, desalination, removal of solvents, and the like.

U.S. Pat. No. 4,837,076 to McCullough et al, which is herewith incorporated by reference discloses a class of carbonaceous fibers which may be used in the present invention.

U.S. Pat. No. 4,744,806 to Ozolins et al, which is herewith incorporated by reference, discloses demister pads and apparatus which are similar to the apparatuses and pads of the invention except that the pads are metallic and cannot be used with an electrical field for separation.

The carbonaceous fibers of the invention according to the test method of ASTM D 2863-77 have an LOI value greater than 40. The test method is also known as "oxygen index" or "limited oxygen index" (LOI). With this procedure the concentration of oxygen in $O_2/N_2$ mixtures is determined at which a vertically mounted specimen is ignited at its upper end and just continues to burn. The size of the specimen is $0.65 \times 0.3$ cm with a length from 7 to 15 cm. The LOI value is calculated according to the equation:

$$LOI = \frac{[O_2]}{[O_2 + N_2]} \times 100$$

The LOI values of different materials are as follows:

| | |
|---|---|
| polypropylene | 17.4 |
| polyethylene | 17.4 |
| polystyrene | 1.1 |
| rayon | 18.6 |
| cotton | 20.1 |
| nylon | 20.0 |
| polycarbonate | 22 |
| rigid polyvinyl chloride | 40 |
| stabilized polyacrylonitrile | 40 |
| graphite | 55 |

The term "non-graphitic" as used herein relates to those carbonaceous fibers having an elemental carbon content of less than 98%, preferably, less than 92%, as further defined in U.S. Pat. No. 4,005,183, which is herein incorporated by reference.

The term "carbonaceous fibers" refers to fibers having a carbon content of at least 65% after an irreversible chemical change brought about by heat treatment as disclosed in U.S. Pat. No. 4,837,076.

SUMMARY OF THE INVENTION

According to the present invention there is provided an improved fibrous element for apparatuses having a fibrous element which is used for separating fluids or non-biotechnological products in solution. The improved fibrous element of the invention comprises non-flammable irreversibly heat set non-graphitic carbonaceous polymeric fibers having an LOI greater than 40. The fibers may be in the form of a batting, matting, webbing or felt, a woven or non-woven fabric, knitted cloth or the like depending upon the particular apparatus in which they are utilized.

The carbonaceous fibers have a carbon content of at least 65% and an aspect ratio (length/diameter; l/d) of greater than 10:1. The fibers may be linear, non-linear or a combination of linear and non-linear fibers. The non-linear fibers are resilient, shape reforming and have a reversible deflection greater than about 1.2:1.

The fibrous elements comprising the carbonaceous fiber of the invention may be separators for gas-liquid, gas-gas, or liquid-liquid systems and solutions containing large molecules.

What is meant by biotechnological products are natural products including those prepared by fermentations, microorganisms, yeasts, and the like. It should also be understood that the term "large molecules" is intended to mean non-biotechnological products.

The fibrous element may comprise regions of high density and low density areas for separation of liquids from a gas stream and for the separation of molecules using electrophoresis type of separation techniques. The different density areas can be achieved by varying the aspect ratios (l/d), using carbonaceous fibers of different heat treatment, using fabrics of different weaves, etc.

Similarly, the fibrous element may comprise layers of carbonaceous fibers having different electrical conductivities. This type of arrangement is particularly suitable for the separation of large molecules having different molecular weight and electrical charges where the separation is the result of an induced electrical field.

The invention will be described for the purposes of illustration only in connection with certain embodiments; however, it is recognized that various changes, modifications, additions and improvements may be made in the illustrated embodiment by those persons skilled in the art without departing from the spirit and scope of the invention.

DESCRIPTION OF THE EMBODIMENTS

Figure 1:
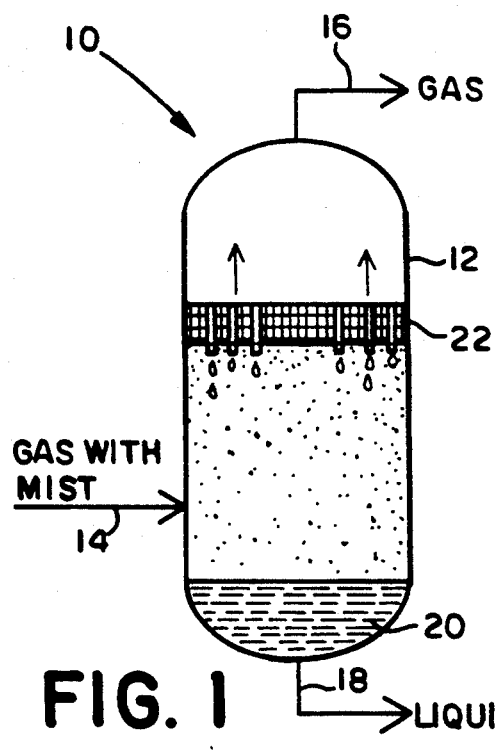
FIG. 1 is an illustrative sectional view of a gas-liquid contact tower containing a layer of the carbonaceous fiber as the fibrous element which is the mist eliminator.

FIG. 1 shows of a gas-liquid contacting system 10 which comprises a gas-liquid contact tower 12 having an inlet at the lower portion thereof 14 for the introduction of a mist-laden gas stream in which the mist particles are to be removed, and an upper portion 16 for the removal of coalesced liquid 20 from the gas-liquid tower 12. Across the diameter of the tower is shown a variegated density, mist eliminator pad of carbonaceous fibers 22 which pad is placed in the gas flow path of the mist-containing gas stream, and is a cylindrical, spiral-wound mesh pad 22, spiral-wound to the dimensions of the gas-liquid contact tower 12.

Figure 2:
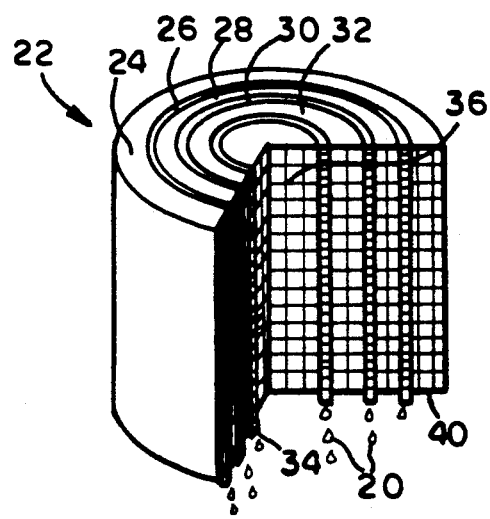
FIG. 2 is an enlarged perspective partial sectional view of the mist eliminator of FIG. 1, and, FIG. 3 is an illustrative sectional view of a separation tower with different layers of carbonaceous fibers.

FIGS. 2 is an enlarged view of the pad 22 showing high density layers 26, 30 and 34 providing a plurality of spiral-wound, higher density regions, e.g. two to six or three as illustrated, and layers 24, 28, 32 and 36 providing a plurality of low-density regions, e.g. two to six or four as illustrated. The high density regions provide for the coalescing and drainage of coalesced liquid 20. As illustrated, the high density region may extend slightly downward from the upstream face 40 of the mesh pad to promote more rapid drainage from the mesh pad.

Figure 3:
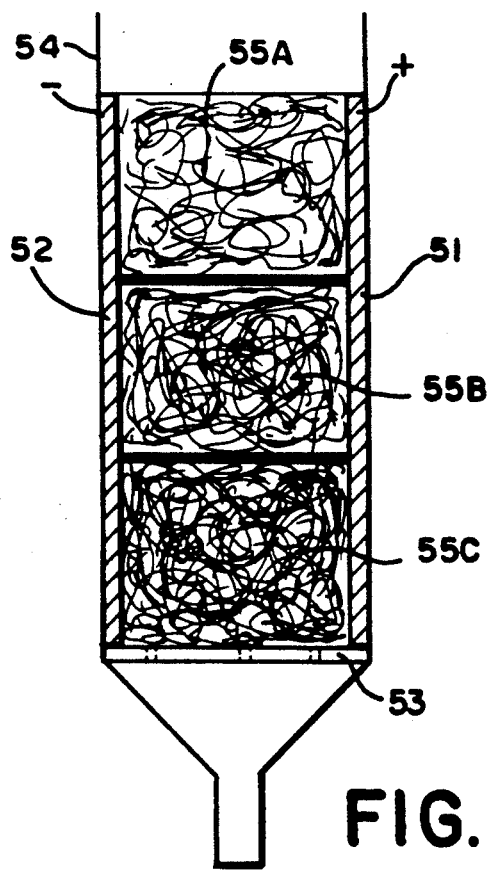

FIG. 3 illustrates a separation column 50 in its simplest form. The separation column is composed of a tower 54 having an aperture disk 53 near its bottom and a pair of electrodes 51, 52 along the sides which provide an electrical charge. Within the column 50 there is placed layers 55A, 55B, 55C of carbonaceous fibers of different electrical conductivities and/or densities. The electrodes 51, 52 create an electrical field through the carbonaceous fibers which affect the migration of different molecules through the column.

The separation column can be used in purification procedures for a large group of non-biotechnological chemical compounds including the removal of by-products of chemical reactions, removal of impurities from liquids, desalination, and the like.

The carbonaceous fibers used in the invention are prepared by heat treating a suitable stabilized carbonaceous precursor material which can be made into carbonaceous fibers or filaments and which are thermally stable. A suitable precursor material may be, for example, derived from a stabilized polymeric material or stabilized pitch (petroleum or coal tar) based materials. Preferably, the precursor material used in the present invention is derived from stabilized acrylic based filaments.

The term "stabilized" as used herein applies to fibers or tows which have been oxidized at a specific temperature, typically less then about 250 degrees Celsius for acrylic fibers. It will be understood that in some instances the filament and/or fibers are oxidized by chemical oxidants at lower temperatures.

The acrylic filaments which are advantageously utilized in preparing the carbonaceous fibers are selected from acrylonitrile homopolymers, acrylonitrile copolymers and acrylonitrile terpolymers. The copolymers preferably contain at least about 85 mole percent of acrylonitrile units and up to 15 mole percent of one or more monovinyl units copolymerized with styrene, methylacrylate, methyl methacrylate, vinyl chloride, vinylidene chloride, vinyl pyridine, and the like. Also, the acrylic filaments may comprise terpolymers, preferably, wherein the acrylonitrile units are at least about 85 mole percent.

The preferred precursor materials are in the form of a monofilament fiber or a plurality of fibers such as a two, or a yarn, a woven fabric, or a knitted cloth which are prepared by any of a number of commercially available techniques. The precursor material in the aforementioned form is heated to a temperature above about 525 degrees Celsius, preferably to above about 550 degrees Celsius. Where the material is in the form of a fabric or cloth is deknitted and carded, following the heat treatment, to produce a wool-like fluff of the carbonaceous fibers which can be laid up in the form of a batting, or the like.

In one embodiment of the present invention, the fibers are polyacrylonitrile (PAN) based fibers which are formed by conventional methods such as by melt, dry or wet spinning a suitable fluid of the precursor material. The fibers, which have a normal diameter of from 4 to 25 micrometers, are collected as an assembly of a multiplicity of continuous filaments, usually 3000 or 6000 individual filaments, in tows. The fibers are then stabilized, for example, by oxidation or any other conventional method of stabilization. The stabilized tows (or staple yarn made from chopped or stretch broken fiber staple) are thereafter formed into a sinusoidal form by knitting the tow or yarn into a fabric or cloth, recognizing that other shape forming methods, such as crimping and coil forming, combined with thermosetting, can be employed to produce a nonlinear shape, for example, as disclosed application Ser. No. 340,098 and 340,099 of McCullough et al., which are now U.S. Pat. Nos. 4,979,274 and 4,977,654.

As disclosed in U.S. Pat. No. 4,837,076, the so formed knitted fabric or cloth is heat treated, in a relaxed and unstressed condition, in a temperature zone of from 525 degrees Celsius to 750 degrees Celsius, in an inert atmosphere, for a period of time to produce a heat induced thermoset reaction wherein additional cross-linking and/or a cross-chain cyclization reaction occurs between the original polymer chain and a desired electrical conductivity is obtained. At a lower temperature range of from 150 degrees Celsius to 525 degrees Celsius, the fibers are provided with a varying proportion of temporary to permanent set, while in an upper range of temperatures of from 525 degrees Celsius and above, the fibers are provided with a substantially permanent or irreversible heat set. The heat treated fabric or cloth may be deknitted, if desired, to produce a tow or yarn containing the nonlinear fibers.

The term "permanent" or "irreversibly heat set" as used herein applies to nonlinear carbonaceous fibers which have been heat treated until they possess a degree of irreversibility where the fibers, when stretched to a substantially linear shape, without exceeding their internal tensile strength, will substantially revert to their original nonlinear shape once the stress on the fibers is released.

It is, of course, to be understood that the fiber assembly may be initially heat treated at the higher range of temperatures so long as the heat treatment is conducted while the nonlinear fibers are in a relaxed or unstressed state, and under an inert, nonoxidizing atmosphere For example, as a result of the higher temperature treatment of 525 degrees Celsius and above, for a set period of time, a substantially irreversible heat set sinusoidal or coil-like configuration or structure is imparted to the fiber assembly which may be used per se or the fiber assembly may be opened to form a wool-like fluff. A number of methods known in the art can be used to create an opening, a procedure in which the yarn, tow, or the fibers or filaments of the cloth are separated into a nonlinear, entangled, wool-like fluffy material in which the individual fibers retain their coil-like or sinusoidal configuration, yielding a fluff or batting-like body of considerable loft. The density of the material can be controlled by the degree of entanglement to produce anywhere from low density, high loft material to a high density material able to produce significant pressure drops of gases flowing through said fluff.

It is to be further understood that carbonaceous precursor starting materials may have imparted to them electrically conductive properties on the order of that of metallic conductors by heating the fiber assembly to a temperature above about 1000 degrees Celsius in a nonoxidizing atmosphere. The electroconductive property may be obtained from selected starting materials such as pitch (petroleum or coal tar), polyacetylene, acrylonitrile based materials, (PANOX TM, a trademark of R.K. Textiles Composite Fibers, Ltd.), polyphenylene, polyvinylidene chloride resin (SARAN TM, a trademark of The Dow Chemical Company), aramids, polybenzimidazoles, polyvinyl halides, and the like.

The carbonaceous fibers derived from acrylonitrile based materials which is utilized in the invention may be classified into three groups.

In a first group, the carbonaceous fibers have a carbon content of greater than 65 percent but less than 85 percent, are electrically nonconductive, and do not possess any electrostatic dissipating characteristics, i.e., they are not able to dissipate an electrostatic charge.

The term electrically nonconductive as utilized in the present invention relates to a resistance of greater than $4 \times 10^6$ ohms/cm when measured on a 6K (6000 filaments) tow of individual fibers having a diameter of from 4 to 20 microns. The preferred fibers of this group have an elongation of about 3 to 9 percent and a tenacity of about 2 to 6 g/d.

When the fiber is a stabilized and heat set acrylic fiber it has been found that a nitrogen content of 18 percent or higher results in an electrically nonconductive fiber.

In a second group, the carbonaceous fibers are classified as being partially electrically conductive (i.e., having a low conductivity) and having a carbon content of greater than 65 percent but less than 85 percent. Low conductivity means that a 6K tow of fibers in which the individual precursor fibers have a diameter of from 4 to 20 micrometer, has a resistance of from $4 \times 10^6$ to $4 \times 10^3$ ohms/cm.

The preferred fibers of this group have an elongation of about 3 to 6 percent and a tenacity of from about 3 to 7 g/d.

In a third group are the fibers having a carbon content of at least 85 percent but less than 98%, preferably, less than 92%. These fibers are characterized as having a high electroconductivity. That is, the fibers are substantially graphitic and have an electrical resistance of less than $4 \times 10^3$ ohms/cm.

The preferred fibers of the third group have an elongation of about 2 to 4% and a tenacity of about 4 to 9 g/d.

The carbonaceous fibers employed in the present invention may be used in substantially any desired fabricated form depending on the purpose for which the structure in which they are incorporated is to be used.

In one embodiment, the fiber assembly may be the original irreversibly heat set knitted fabric containing the carbonaceous fibers.

In another embodiment of this invention, the assembly may include the individual carbonaceous fibers in a densified batting of long or short fibers. The carbonaceous fibers generally can be from 3 mm to 12.5 cm in length.

In still another embodiment, the assembly may be carbonaceous fibers used in the form of a yarn or tow composed of many filaments.

In still another embodiment the assembly may be the carbonaceous fibers fabricated into a knitted cloth, for example, plain jersey knit, interlock, ribbed, cross float jersey knit or weft knit and the like, or woven into a fabric, for example of plain weave, satin weave, twill weave, basket weave, and the like. The woven fabric may combine the nonlinear carbonaceous fibers, for example, as warp.

The fiber assembly may also be in the form of a nonwoven material or fabric such as a web, mat, fluff or batting of fibers such as described above. In another embodiment the assembly may include the wool-like fluffy material produced form the thermally set knitted fabric which contains the nonlinear fibers. The assembly in the form of a batting or wool-like fluff may be prepared by conventional needle-punching means.

A densified mat or batting may be prepared by the procedure described in copending patent application Ser. No. 344,327 of McCullough et al, filed Apr. 27, 1989, entitled "Lock Set Structures", which is U.S. Pat. No. 4,902,561 and herein incorporated by reference. Accordingly a densified structure is provided by interlocking the permanently set carbonaceous fibers with similar precursor fibers and heat setting the entire structure. The resulting densified structure then contains carbonaceous fibers of similar electroconductivities throughout.

Also, there is provided a means for interlocking two mats or battings of different carbonaceous fibers so as to form a filter element with varied densities or conductivities.

What is claimed is:

1. In an apparatus for separating fluids, which said apparatus has a fibrous element which permits flow of fluids therethrough and is capable of use in a corrosive atmosphere of non-oxidizing acids, the improvement which comprises said fibrous element being composed of non-graphitic carbonaceous polymeric fibers having an LOI greater than 40, and a carbon content of at least 65% which is the result of an irreversible chemical change whereby an increase of carbon content occurred.

2. The apparatus of claim 1, wherein said fibrous element comprises linear or nonlinear monofilament fibers, a fiber tow, a yarn, a multiplicity of fibers forming a wool-like fluff, a nonwoven batting, matting, webbing or felt, or a woven fabric or knitted cloth.

3. The apparatus of claim 1, wherein said carbonaceous fibers are nonlinear, resilient, shape reforming and elongatable, have a reversible deflection ratio of greater than 1.2:1.

4. The apparatus of claim 1, wherein the carbonaceous fibers are linear.

5. The device of claim 1, wherein said carbonaceous fibers are derived from stabilized polymeric precursor fibers.

6. The device of claim 5, wherein said polymeric precursor fibers are acrylic fibers selected from acrylonitrile homopolymers, acrylonitrile copolymers and acrylonitrile terpolymers, wherein said copolymers and terpolymers contain at least 85 mole percent acrylic units and up to 15 mole percent of one or more monovinyl units copolymerized with another polymer.

7. The device of claim 6, wherein said carbonaceous fibers are electrically conductive.

8. The device of claim 4, wherein said carbonaceous fibers are electrically nonconductive or do not possess any electrostatic dissipating characteristics.

9. The device of claim 1, wherein said fibrous element comprises layers of high and low density carbonaceous fibers.

10. The device of claim 1, wherein said fibrous element comprises layers of carbonaceous fibers having different electrical conductivities.

11. The device of claim 1, wherein said fibrous element comprises layers of carbonaceous fibers having high and low density regions and layers of carbonaceous fibers having different electrical conductivities.

12. A method for separating fluids comprising passing a fluid for separation through a fibrous element comprising non-graphitic carbonaceous fibers derived from oxidized polyacrylonitrile fibers having an electrical conductivity and an LOI greater than 40 and a carbon content of at least 65% which is the result of an irreversible chemical change whereby an increase of carbon content occurred, and passing an electrical current through said fibrous element so as to affect migration of the fluids.

13. The method of claim 12, wherein said fibrous element comprises layers of carbonaceous fibers having different electrical conductivity.

14. The method of claim 12, wherein said fibrous element comprises layers of carbonaceous fibers providing different density regions.

15. The method of claim 12, wherein said fibrous element is comprised of high and low density regions and layers of carbonaceous fibers having different electrical conductivities.

16. The method of claim 12 wherein said fluid comprises non-biotechnical products.

17. The method of claim 12 wherein solids are separated from said fluid.

* * * * *